United States Patent
Nakagawa et al.

(10) Patent No.: US 11,827,603 B2
(45) Date of Patent: Nov. 28, 2023

(54) METHOD FOR PREPARING 1-(1-TERT-BUTOXYCARBONYL-4-PIPERIDYLACETYL)-4-MESYLOXY-PIPERIDINE AND 1-(1-TERT-BUTOXYCARBONYL-4-PIPERIDYLACETYL)-4-MESYLOXY-PIPERIDINE

(71) Applicant: YUKI GOSEI KOGYO CO., LTD., Tokyo (JP)

(72) Inventors: Kiyono Nakagawa, Tokyo (JP); Yoshihiro Ito, Tokyo (JP); Hirohisa Kitahara, Tokyo (JP)

(73) Assignee: YUKI GOSEI KOGYO CO., LTD., Tokyo (JP)

( * ) Notice: Subject to any disclaimer, the term of this patent is extended or adjusted under 35 U.S.C. 154(b) by 741 days.

(21) Appl. No.: 16/962,397

(22) PCT Filed: Jan. 18, 2019

(86) PCT No.: PCT/JP2019/001427
§ 371 (c)(1),
(2) Date: Dec. 16, 2020

(87) PCT Pub. No.: WO2019/142901
PCT Pub. Date: Jul. 25, 2019

(65) Prior Publication Data
US 2022/0388959 A1    Dec. 8, 2022

(30) Foreign Application Priority Data
Jan. 19, 2018  (JP) .................. 2018-007428

(51) Int. Cl.
C07D 211/70    (2006.01)
C07D 211/34    (2006.01)
C07D 211/46    (2006.01)

(52) U.S. Cl.
CPC .......... *C07D 211/70* (2013.01); *C07D 211/34* (2013.01); *C07D 211/46* (2013.01)

(58) Field of Classification Search
CPC .... C07D 211/70; C07D 211/34; C07D 211/46
See application file for complete search history.

(56) References Cited

U.S. PATENT DOCUMENTS

| | | | |
|---|---|---|---|
| 4,695,575 A | 9/1987 | Janssens et al. | |
| 2004/0063953 A1* | 4/2004 | Nakagawa | C07D 211/46 546/188 |

(Continued)

FOREIGN PATENT DOCUMENTS

| | | |
|---|---|---|
| JP | 2003155287 A | 5/2003 |
| JP | 2004131486 A | 4/2004 |

(Continued)

OTHER PUBLICATIONS

International Search Report (and English translation) and Written Opinion of the International Searching Authority for PCT/JP2019/001427 dated Mar. 12, 2019.

(Continued)

*Primary Examiner* — Timothy R Rozof
(74) *Attorney, Agent, or Firm* — Heslin Rothenberg Farley & Mesiti P.C.

(57) ABSTRACT

The object of the present invention is to provide 1-(1-tert-butoxycarbonyl-4-piperidylacetyl)-4-mesyloxypiperidine having a low content of impurities The object can be solved by a method for preparing 1-(1-benzyl-4-piperidylacetyl)-4-hydroxypiperidine, comprising the steps of:
(1) reductively reacting 1-benzyl-4-piperidylidene acetic acid ethyl ester represented by the formula [1]:

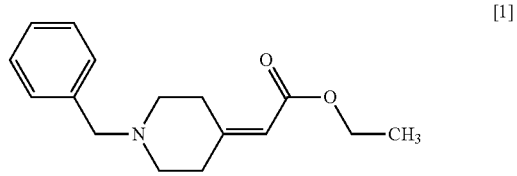

to obtain 1-benzyl-4-piperidyl acetic acid ethyl ester represented by the formula [2]:

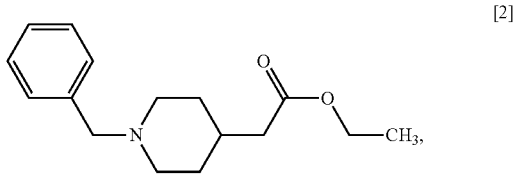

(2) adding an ammonium chloride aqueous solution and an organic solvent to the liquid containing 1-benzyl-4-piperidyl acetic acid ethyl ester, mixing the whole, and separating into an organic layer and an aqueous layer, (3) collecting 1-benzyl-4-piperidyl acetic acid ethyl ester from the organic layer, and (4) reacting the obtained 1-benzyl-4-piperidyl acetic acid ethyl ester with 4-hydroxypiperidine represented by the formula [3]:

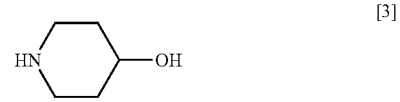

in the presence of base, to obtain 1-(1-benzyl-4-piperidy-lacetyl)-4-hydroxypiperidine represented by the formula [4]:

(Continued)

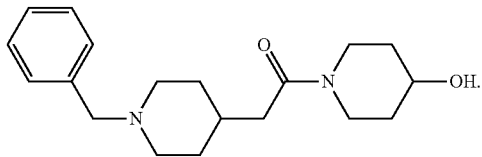

7 Claims, No Drawings

(56) References Cited

U.S. PATENT DOCUMENTS

| | | |
|---|---|---|
| 2004/0122232 A1 | 6/2004 | Chen et al. |
| 2004/0235865 A1 | 11/2004 | Ikegami |
| 2006/0074241 A1 | 4/2006 | Chen et al. |
| 2010/0234395 A1* | 9/2010 | Sugawara ............... A61P 25/04 546/210 |
| 2011/0009389 A1 | 1/2011 | Kubo et al. |

FOREIGN PATENT DOCUMENTS

| | | |
|---|---|---|
| JP | 2004182730 A | 7/2004 |
| JP | 2005179351 A | 7/2005 |
| JP | 2006104130 A | 4/2006 |
| JP | 2006511481 A | 4/2006 |
| WO | 0059503 A1 | 10/2000 |
| WO | 2004/031153 A2 | 4/2004 |
| WO | 2007/111323 A1 | 10/2007 |

OTHER PUBLICATIONS

Extended European Search Report in EP 19741616.7, dated Sep. 16, 2021.

* cited by examiner

METHOD FOR PREPARING 1-(1-TERT-BUTOXYCARBONYL-4-PIPERIDYLACETYL)-4-MESYLOXY-PIPERIDINE AND 1-(1-TERT-BUTOXYCARBONYL-4-PIPERIDYLACETYL)-4-MESYLOXY-PIPERIDINE

TECHNICAL FIELD

The present invention relates to a method for preparing 1-(1-tert-butoxycarbonyl-4-piperidylacetyl)-4-mesyloxypiperidine. According to the present invention, 1-(1-tert-butoxycarbonyl-4-piperidylacetyl)-4-mesyloxypiperidine wherein the amount of by-product (i.e. (1-(1-tert-butoxycarbonyl-4-piperidylacetyl)-4-(2-(4-mesyloxypiperidine-1-yl)-2-oxyethyl) piperidine) is extremely few, can be prepared.

BACKGROUND ART 1-(1-tert-butoxycarbonyl-4-piperidylacetyl)-4-mesyloxypiperidine is useful, for example, as an intermediate for synthesizing farnesyl protein transferase inhibitor (Patent literature 1).

As a method for preparing 1-(1-tert-butoxycarbonyl-4-piperidylacetyl)-4-mesyloxypiperidine, it is disclosed that N-aralkylpiperidine derivative (for example, 1-(1-benzyl-4-piperidylacetyl)-4-hydroxypiperidine) is reacted with mesyl halide (mesyl chloride) in the presence of base, and the obtained mesyl compound (1-(1-benzyl-4-piperidylacetyl)-4-mesyloxypiperidine) is reacted with di-tert-butyl dicarbonate in the presence of hydrogen and a catalyst containing palladium, to thereby obtain 1-(1-tert-butoxycarbonyl-4-piperidylacetyl)-4-mesyloxypiperidine (Patent literature 2).

CITATION LIST

Patent Literature

[Patent literature 1] Japanese Translation Publication (Kohyo) No. 2006-511481
[Patent literature 2] Japanese Unexamined Patent Publication (Kokai) No. 2004-131486

SUMMARY OF INVENTION

Technical Problem

The present inventors had prepared 1-(1-tert-butoxycarbonyl-4-piperidylacetyl)-4-mesyloxypiperidine (hereinafter, sometimes referred to as PAA-MPN) by the method described in Patent literature 2, and as a result, found that a slight amount of (1-(1-tert-butoxycarbonyl-4-piperidylacetyl)-4-(2-(4-mesyloxypiperidine-1-yl)-2-oxyethyl) piperidine (hereinafter, sometimes referred to as WPA-MPN) was contained as an impurity therein.

As mentioned above, 1-(1-tert-butoxycarbonyl-4-piperidylacetyl) mesyloxypiperidine is used as the intermediate for synthesizing medicine. Therefore, it is preferable that the amount of impurities contained in 1-(1-tert-butoxycarbonyl piperidylacetyl)-4-mesyloxypiperidine is as small as possible.

Accordingly, the object of the present invention is to provide 1-(1-tert-butoxycarbonyl-4-piperidylacetyl)-4-mesyloxypiperidine having a low content of impurities.

Solution to Problem

The present inventors have conducted intensive studies on 1-(1-tert-butoxycarbonyl-4-piperidylacetyl)-4-mesyloxypiperidine(PAA-MPN) having a low content of impurities.

In the method for preparing PAA-MPN described in Patent literature 2, specifically, PAA-MPN is synthesized by a step (I) of reacting 1-benzyl-4-piperidone (hereinafter, sometimes referred to as 1-BPD) with ethyl diethylphosphonoacetate (hereinafter, sometimes referred to as EDEPA) in the presence of base, a step (II) of reductively reacting the obtained 1-benzyl-4-piperidylidene acetic acid ethyl ester (hereinafter, sometimes referred to as 1-BPDE), a step (III) of reacting the obtained 1-benzyl-4-piperidyl acetic acid ethyl ester (hereinafter, sometimes referred to as 1-BPAE) with 4-hydroxypiperidine (hereinafter, sometimes referred to as 4-HPPN) in the presence of base, a step (IV) of reacting 1-(1-benzyl-4-piperidylacetyl)-4-hydroxypiperidine (hereinafter, sometimes referred to as BnPA-H) with mesyl chloride, and a step (V) of reacting the obtained 1-(1-benzyl-4-piperidylacetyl)-4-mesyloxypiperidine (hereinafter, sometimes referred to as BnPA-M) with di-tert-butyl dicarbonate.

The present inventors surprisingly found that by-product, i.e. WPA-MPN, contained in PAA-MPN is dramatically reduced by extracting and separating 1-BPAE obtained in the step (II) with an ammonium chloride aqueous solution and an organic solvent, and by using the extracted 1-BPAE in step (III).

The present invention is based on the above findings.

Accordingly, the present invention relates to

[1] a method for preparing 1-(1-benzyl-4-piperidylacetyl)-4-hydroxypiperidine, comprising the steps of:

(1) reductively reacting 1-benzyl-4-piperidylidene acetic acid ethyl ester represented by the formula [1]:

[Chem. 1]

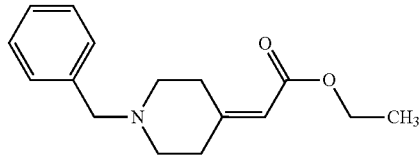

[1]

to obtain 1-benzyl-4-piperidyl acetic acid ethyl ester represented by the formula [2]:

[Chem. 2]

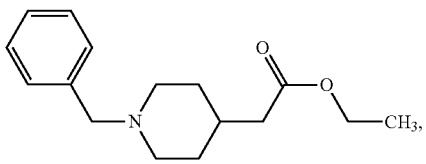

[2]

(2) adding an ammonium chloride aqueous solution and an organic solvent to a liquid containing 1-benzyl-4-piperidyl acetic acid ethyl ester, mixing the whole, and separating into an organic layer and an aqueous layer, (3) collecting 1-benzyl-4-piperidyl acetic acid ethyl ester from the organic layer, and (4) reacting the obtained 1-benzyl-4-piperidyl acetic acid ethyl ester with 4-hydroxypiperidine represented by the formula [3]:

[Chem. 3]

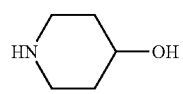

in the presence of base, to obtain 1-(1-benzyl-4-piperidy-lacetyl)-4-hydroxypiperidine represented by the formula [4]:

[Chem. 4]

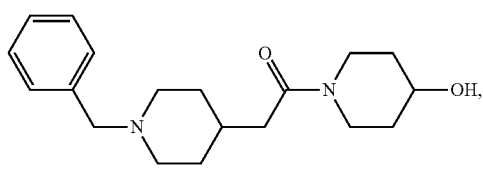

[2] the method for preparing 1-(1-benzyl-4-piperidy-lacetyl)-4-hydroxypiperidine of the item [1], wherein the organic solvent is selected from the group consisting of a hydrocarbon-based organic solvent, an ester-based organic solvent, an ether-based organic solvent, and halogen-based organic solvent,

[3] a method for preparing 1-(1-tert-butoxycarbonyl-4-piperidylacetyl)-4-mesyloxypiperidine, comprising the steps of:

steps (1) to (4) according to claim 1, and (5) reacting 1-(1-benzyl-4-piperidylacetyl)-4-hydroxypiperidine obtained in the step (4) with mesyl chloride in the presence of base, to obtain 1-(1-benzyl-4-piperidy-lacetyl)-4-mesyloxypiperidine represented by the formula [5]:

[Chem. 5]

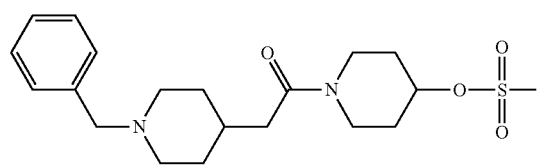

and (6) reacting the 1-(1-benzyl-4-piperidylacetyl)-4-mesy-loxypiperidine with di-tert-butyl dicarbonate in the presence of hydrogen and a catalyst containing palladium, to obtain 1-(1-tert-butoxycarbonyl-4-piperidy-lacetyl)-4-mesyloxypiperidine represented by the formula [6]:

[Chem. 6]

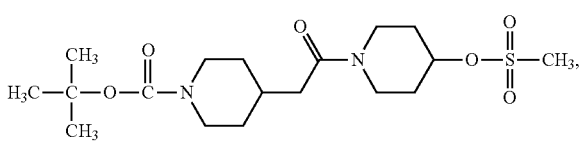

[4] The method for preparing 1-(1-tert-butoxycarbonyl-4-piperidylacetyl) mesyloxypiperidine of the item [3], wherein the organic solvent is selected from the group consisting of a hydrocarbon-based organic solvent, an ester-based organic solvent, an ether-based organic solvent, and halogen-based organic solvent,

[5] a method for collecting 1-benzyl-4-piperidyl acetic acid ethyl ester, comprising the steps of:

(1) reductively reacting 1-benzyl-4-piperidylidene acetic acid ethyl ester represented by the formula [1]:

[Chem. 7]

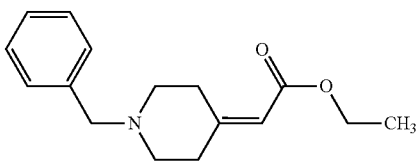

to obtain 1-benzyl-4-piperidyl acetic acid ethyl ester represented by the formula [2]:

[Chem. 8]

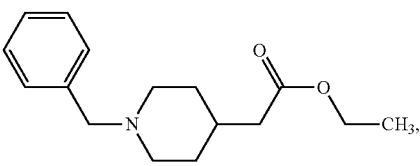

(2) adding an ammonium chloride aqueous solution and an organic solvent to the reaction mixture of 1-benzyl-4-piperidyl acetic acid ethyl ester, mixing the whole, and separating into an organic layer and an aqueous layer, and (3) collecting 1-benzyl-4-piperidyl acetic acid ethyl ester from the organic layer,

[6] the method for collecting 1-benzyl-4-piperidyl acetic acid ethyl ester of the item [5], wherein the organic solvent is selected from the group consisting of a hydrocarbon-based organic solvent, an ester-based organic solvent, an ether-based organic solvent, and halogen-based organic solvent, and

[7] 1-(1-tert-butoxycarbonyl-4-piperidylacetyl)-4-mesy-loxypiperidine represented by the formula [6]:

[Chem. 10]

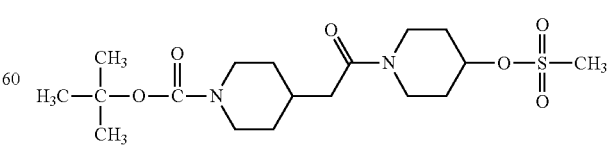

wherein a content of (1-(1-tert-butoxycarbonyl-4-piperidy-lacetyl)-4-(2-(4-mesyloxypiperidine-1-yl)-2-oxyethyl) piperidine represented by the formula [7]:

[Chem. 9]

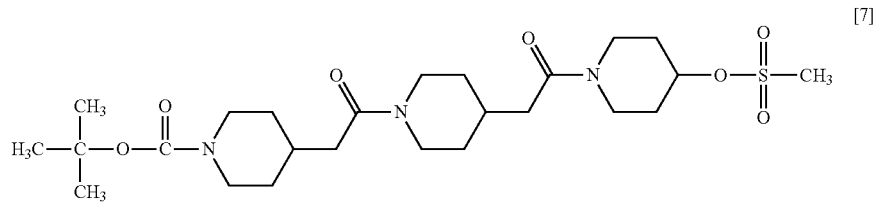

[7]

is 1.0% or less.

Advantageous Effects of Invention

According to the method for preparing 1-(1-tert-butoxycarbonyl piperidylacetyl)-4-mesyloxypiperidine, 1-(1-tert-butoxycarbonyl-4-piperidylacetyl) mesyloxypiperidine wherein the amount of by-product (i.e. (1-(1-tert-butoxycarbonyl piperidylacetyl)-4-(2-(4-mesyloxypiperidine-1-yl)-2-oxyethyl) piperidine) is extremely few, can be prepared.

DESCRIPTION OF EMBODIMENTS

[1] Method for Preparing 1-(1-tert-butoxycarbonyl-4-piperidylacetyl)-4-mesyloxypiperidine The method for preparing 1-(1-tert-butoxycarbonyl-4-piperidylacetyl)-4-mesyloxypiperidine comprises:
(1) a step of reductively reacting 1-benzyl-4-piperidylidene acetic acid ethyl ester to obtain 1-benzyl-4-piperidyl acetic acid ethyl ester,
(2) a step of adding an ammonium chloride aqueous solution and an organic solvent to the liquid containing 1-benzyl-4-piperidyl acetic acid ethyl ester, mixing the whole, and separating into an organic layer and an aqueous layer,
(3) a step of collecting 1-benzyl-4-piperidyl acetic acid ethyl ester from the organic layer,
(4) a step of reacting the obtained 1-benzyl-4-piperidyl acetic acid ethyl ester with 4-hydroxypiperidine in the presence of base, to obtain 1-(1-benzyl-4-piperidylacetyl) 4-hydroxypiperidine,
(5) a step of reacting the obtained 1-(1-benzyl-4-piperidylacetyl)-4-hydroxypiperidine with mesyl chloride in the presence of base, to obtain 1-(1-benzyl-4-piperidylacetyl)-4-mesyloxypiperidine, and
(6) a step of reacting the 1-(1-benzyl-4-piperidylacetyl)-4-mesyloxypiperidine with di-tert-butyl dicarbonate in the presence of hydrogen and a catalyst containing palladium, to obtain 1-(1-tert-butoxycarbonyl-4-piperidylacetyl)-4-mesyloxypiperidine.

1-benzyl-4-piperidylidene acetic acid ethyl ester used in the step (1) may be obtained by a step of reacting 1-benzyl-4-piperidone with ethyl diethylphosphonoacetate in the presence of base, to obtain 1-benzyl-4-piperidylidene acetic acid ethyl ester.

PAA-MPN is prepared by the step (1), and the steps (4) to (6) in the method for preparing PAA-MPN (Patent literature 2). PAA-MPN obtained by the preparation method contains about 1.2% of (1-(1-tert-butoxycarbonyl-4-piperidylacetyl)-4-(2-(4-mesyloxypiperidine-1-yl)-2-oxyethyl) piperidine (WPA-MPN) which is a by-product (Comparative Example 1). The content of WPA-MPN contained in PAA-MPN can be reduced to 1.0% or less by the steps (2) and (3) in the method for preparing PAA-MPN of the present invention.

The concentration of the ammonium chloride aqueous solution in the step (2) is not particularly limited as long as the effect of the present invention can be achieved, but for example, the lower limit of the concentration of the ammonium chloride aqueous solution is 0.5% by weight or more, and more preferably 1% by weight or more, even more preferably 2% by weight or more. The upper limit of the concentration of the ammonium chloride aqueous solution is also not limited, and is 27% by weight (which is the solubility of ammonium chloride at 20° C.) or less, preferably 20% by weight or less, more preferably 15% by weight or less. The upper limit and the lower limit of the concentration of the ammonium chloride aqueous solution can be independently combined, that is, the respective combinations of the upper limit and the lower limit can be the range of the concentration of the ammonium chloride aqueous solution.

The concentration of WPA-MPN contained in PAA-MPN can be sufficiently reduced by using 0.5% by weight or more of the ammonium chloride aqueous solution. For example, it is considered that the concentration of WPA-MPN contained in PAA-MPN can be reduced to less than 0.1% by using a 1% by weight of ammonium chloride aqueous solution.

The pH of the ammonium chloride aqueous solution is not particularly limited as long as the effect of the present invention can be achieved, but for example, the lower limit of pH is 1 or more, and more preferably 1.5 or more. The upper limit is pH 12 or less, more preferably pH 11 or less, even more preferably pH 10 or less, most preferably pH 9 or less.

The organic solvent used in the preparation method of the present invention is not particularly limited as long as it can be separated from the ammonium chloride aqueous solution, but includes, for example, a hydrocarbon-based organic solvent, an ester-based organic solvent, an ether-based organic solvent, a halogen-based organic solvent, or a ketone-based organic solvent.

The hydrocarbon-based organic solvent is not particularly limited, as long as it can dissolve 1-BPAE, but includes aliphatic hydrocarbons, alicyclic hydrocarbons, or aromatic hydrocarbons. As the aliphatic hydrocarbons, there may be mentioned pentane, isopentane, neopentane, hexane, heptane, isoheptane, octane, isooctane, nonane, isononane, decane, undecane, dodecane, or the like. As the alicyclic hydrocarbons, there may be mentioned cyclopentane, methyl cyclopentane, ethyl cyclopentane, cyclohexane, methyl cyclohexane, ethyl cyclohexane, tert-butyl cyclohexane, o-menthane, m-menthane, p-menthane, cycloheptane, cyclooctane, cyclodecane, decalin, or the like. As the aromatic hydrocarbons, there may be mentioned benzene, toluene, ethylbenzene, cumene, o-xylene, m-xylene, p-xylene, diethylbenzene, mesitylene, tetralin, or the like.

The ester-based organic solvent is not particularly limited, as long as it can dissolve 1-BPAE, but includes for example, ethyl acetate, methyl acetate, propyl acetate, butyl acetate, isopropyl acetate, or ethyl propionate.

The ether-based organic solvent is not particularly limited, as long as it can dissolve 1-BPAE, but includes for example, tert-butyl methyl ether (MTBE), diethyl ether, dimethoxy ethane, tetrahydrofuran (THF), dioxane, diisopropylether, dibutyl ether, cyclopentyl methyl ether, or methyltetrahydrofuran, or methyltetrahydropyran.

The halogen-based organic solvent is not particularly limited, as long as it can dissolve 1-BPAE, but includes for example, chloroform, dichloromethane, dichloroethane, carbon tetrachloride, or chlorobenzene.

The ratio of the ammonium chloride aqueous solution to the organic solvent is not particularly limited as long as 1-BPAE can be dissolved in the organic solvent and impurities can be dissolved in the ammonium chloride aqueous solution, but is, for example, 0.05 to 10 parts by volume, preferably 0.1 to 5 parts by volume, more preferably 0.2 to 2 parts by volume, with respect to 1 part by volume of the organic solvent.

Further, the ratio of the total amount of the ammonium chloride aqueous solution and the organic solvent with respect to the liquid containing 1-BPAE is not particularly limited as long as the effects of the present invention can be achieved, but is, for example, 0.5 to 50 parts by volume, preferably 1 to 20 parts by volume, most preferably 2 to 10 parts by volume, with respect to 1 part by volume of the liquid containing 1-BPAE.

Method for Preparing 1-(1-benzyl-4-piperidylacetyl)-4-hydroxypiperidine 1-(1-benzyl-4-piperidylacetyl)-4-hydroxypiperidine can be prepared by the steps (1) to (4) of the method for preparing 1-(1-tert-butoxycarbonyl-4-piperidylacetyl) mesyloxypiperidine of the present invention.

That is to say, the method for preparing 1-(1-benzyl-4-piperidylacetyl) hydroxypiperidine comprises the steps of: (1) reductively reacting 1-benzyl piperidylidene acetic acid ethyl ester represented to obtain 1-benzyl-4-piperidyl acetic acid ethyl ester, (2) adding an ammonium chloride aqueous solution and an organic solvent to the liquid containing 1-benzyl-4-piperidyl acetic acid ethyl ester, mixing the whole, and separating into an organic layer and an aqueous layer, (3) collecting 1-benzyl-4-piperidyl acetic acid ethyl ester from the organic layer, and (4) reacting the obtained 1-benzyl-4-piperidyl acetic acid ethyl ester with 4-hydroxypiperidine in the presence of base, to obtain 1-(1-benzyl-4-piperidylacetyl)-4-hydroxypiperidine.

1-(1-benzyl-4-piperidylacetyl)-4-hydroxypiperidine obtained by the preparation method of the present invention can be availably used as a raw material for PAA-MPN.

Method for Collecting 1-benzyl-4-piperidyl Acetic Acid Ethyl Ester

According to the steps (1) to (3) in the method for preparing 1-(1-tert-butoxycarbonyl-4-piperidylacetyl)-4-mesyloxypiperidine of the present invention, 1-benzyl-4-piperidyl acetic acid ethyl ester can be collected from a reaction mixture containing 4-piperidyl acetic acid ethyl ester (hereinafter, sometimes referred to as EPNA)

That is to say, the method for collecting 1-benzyl-4-piperidyl acetic acid ethyl ester comprises the steps of: (1) reductively reacting 1-benzyl-4-piperidylidene acetic acid ethyl ester to obtain 1-benzyl-4-piperidyl acetic acid ethyl ester, (2) adding an ammonium chloride aqueous solution and an organic solvent to the reaction mixture of 1-benzyl-4-piperidyl acetic acid ethyl ester, mixing the whole, and separating into an organic layer and an aqueous layer, and (3) collecting 1-benzyl-4-piperidyl acetic acid ethyl ester from the organic layer.

[2] 1-(1-tert-butoxycarbonyl-4-piperidylacetyl)-4-mesyloxypiperidine 1-(1-tert-butoxycarbonyl-4-piperidylacetyl)-4-mesyloxypiperidine (PAA-MPN) of the present invention contains (1-(1-tert-butoxycarbonyl-4-piperidylacetyl)-4-(2-(4-mesyloxypiperidine-1-yl)-2-oxyethyl) piperidine(WPA-MPN) in a content of 1.0% by weight or less.

The content of WPA-MPN is preferably 0.8% or less, more preferably 0.5% or less, and most preferably 0.1% or less. The content of WPA-MPN is calculated from the area ratio of the analysis by liquid chromatography. Specifically, the content of WPA-MPN can be shown by the area percentage of PAA-MPN obtained by liquid chromatography

[Chem. 11]

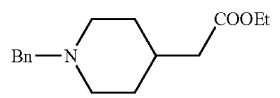 + 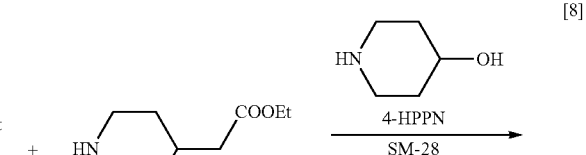

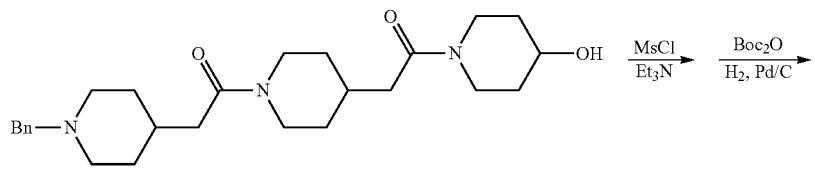

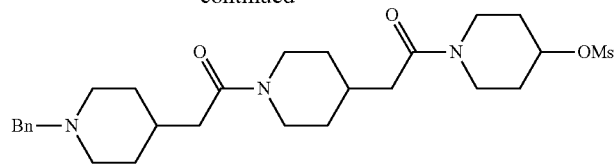

«Function»

The mechanism of the few content of (1-(1-tert-butoxycarbonyl piperidylacetyl)-4-(2-(4-mesyloxypiperidine-1-yl)-2-oxyethyl) piperidine (WPA-MPN) as a by-product in 1-(1-tert-butoxycarbonyl-4-piperidylacetyl)-4-mesyloxypiperidine (PAA-MPN) obtained by the preparation method of the present invention is presumed as follows. However, the present invention is by no means limited to the following presumption.

According the method described in Patent literature 2, PAA-MPN is synthesized by a step of reacting 1-BPD with EDEPA in the presence of base, a step of reductively reacting the obtained 1-BPDE, a step of reacting the obtained 1-BPAE with 4-HPPN in the presence of base, a step of reacting BnPA-H with mesyl chloride, and a step of reacting the obtained BnPA-M with di-tert-butyl dicarbonate in the presence of hydrogen and a catalyst containing palladium. The present inventors presumed that the by-product i.e. WPA-MPN is produced as follows. As shown in reaction scheme [8], 4-piperidyl acetic acid ethyl ester (EPNA) is by-produced by excessive reduction of the benzyl group of 1-BPDE in the step of reducing 1-BPDE. EPNA reacts with 4-HPPN to obtain 1-(1-benzyl-4-piperidylacetyl)-4-(2-(4-hydroxypiperidine-1-yl)-2-oxyethyl)piperidine, and then WPA-MPN is prepared thereby.

In the conventional preparation method, EPNA was not removed. Therefore, it is considered that WPA-MPN was mixed as a by-product in PAA-MPN (final product) by the above reaction step. Furthermore, even if PAA-MPN is prepared by a synthesis method other than the method of Patent literature 2, WPA-MPN may be mixed as a by-product when similar precursors are mixed in preparation steps.

EXAMPLES

The present invention will now be further illustrated by, but is by no means limited to, the following Examples.

Example 1

Synthesis of 1-(1-tert-butoxycarbonyl-4-piperidyl acetyl)-4-mesyloxypiperidine (PAA-MPN)

Synthesis step of 1-benzyl-4-piperidylidene Acetic Acid Ethyl Ester

To a mixture of ethyl diethylphosphonoacetate (235.4 g; 1.05 mol), toluene (618 g), and ethanol solution containing

[Chem. 11]

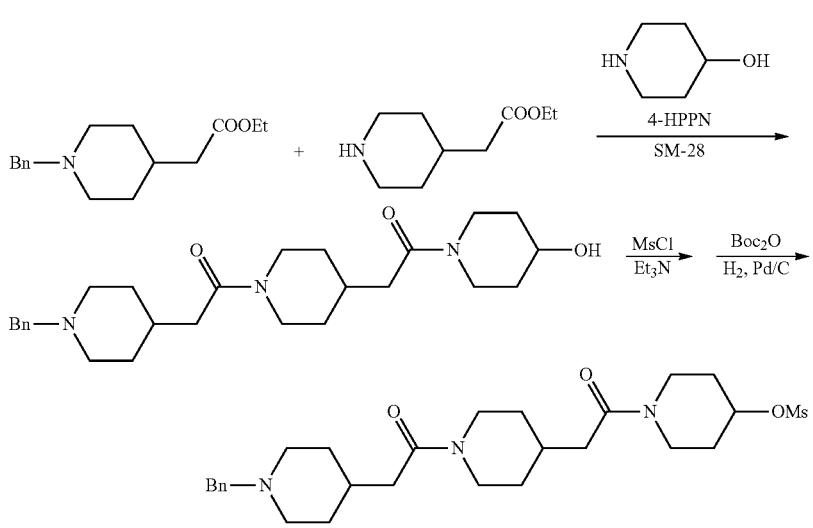

As shown in the examples, the present inventors have found that 1-BPAE obtained after the reduction reaction step of 1-BPDE contains a few amount of EPNA. Therefore, it is presumed that by removing EPNA after the 1-BPDE reduction step, the production of by-product, i.e. WPA-MPN is suppressed, and the amount of WPA-MPN contained in PAA-MPN is suppressed.

20% sodium ethoxide (374.3 g; 1.10 mol in terms of sodium ethoxide), a mixed solution of 1-benzyl-4-piperidone (189.3 g; 1.00 mol) and toluene (190 g) was added dropwise at 5 to 15° C. After reacting at the same temperature for 1 hour, the reaction mixture was washed with water three times at room temperature. The organic layer was dried with anhydrous magnesium sulfate and then concentrated under reduced pressure to obtain 247.2 g of the above-referenced compound as an orange oily residue (yield 95.3%).

Step 1

Synthesis of 1-benzyl-4-piperidyl Acetic Acid Ethyl Ester(1-BPAE)

1-benzyl-4-piperidylidene acetic acid ethyl ester (310 g; 1.195 mol), 2-propanol (1623 g), and 3% platinum-carbon (31 g) containing 50% water were applied to a four-necked reaction flask (volume of 5 L), and mixed. Hydrogen was added at normal pressure while bubbling, and the mixture was reacted at 55° C. for 5 hours. The obtained reaction mixture was cooled to room temperature, and the catalyst was filtered off. The filtrate was concentrated under reduced pressure to obtain 286 g of the above-referenced compound as a pale yellow oily residue (yield: 91%).

Steps 2 and 3

Toluene (98 g) and 5% ammonium chloride aqueous solution (48 g) were added to 1-benzyl-4-piperidyl acetic acid ethyl ester(1-BPAE) (24.6 g; 0.094 mol) obtained in step 1 of Example 1, and mixed. The toluene layer and the aqueous layer were separated, and the toluene layer was collected.

Step 4

Synthesis of 1-(1-benzyl-4-piperidylacetyl)-4-hydroxypiperidine

The toluene solution of 1-benzyl-4-piperidyl acetic acid ethyl ester (122 g; containing 24.6 g (0.094 mol) of 1-benzyl-4-piperidyl acetic acid ethyl ester), 4-hydroxypiperidine (10.0 g; 0.099 mol), and 28% sodium methoxide (9.1 g; 0.047 mol in terms of sodium methoxide) were applied to a four-necked reaction flask (volume of 300 mL), and mixed. 78 g of the solvent was distilled off under normal pressure, and then the mixture was refluxed for 3 hours at an internal temperature of 107° C. After completion of the reaction, the reaction mixture was cooled to 50° C. and washed with brine and 10% HCl water to obtain a toluene solution of the above-referenced compound.

Step 5

Synthesis of 1-(1-benzyl-4-piperidylacetyl)-4-mesyloxypiperidine

Toluene (214 g), the solution of 1-(1-benzyl-4-piperidylacetyl)-4-hydroxypiperidine in toluene (84 g; containing 29.8 g (0.094 mol) of BnPA-H) obtained in step 4, and triethylamine (12.4 g; 0.122 mol) were applied to a four-necked reaction flask (volume of 300 mL). After cooling to 10° C. or less, mesyl chloride (10.8 g; 0.094 mol) was added dropwise at 0 to 10° C., and the mixture was reacted at the same temperature for 1 hour. After the reaction was completed, the mixture was washed with a sodium hydrogen carbonate aqueous solution and brine to obtain an organic layer. The obtained organic layer was concentrated under reduced pressure. It was precipitated from 2-propanol and subjected to solid-liquid separation, to obtain 30.2 g of the above-referenced compound as a white powder (yield: 81.8%).

Step 6

Synthesis of 1-(1-tert-butoxycarbonyl-4-piperidylacetyl)-4-mesyloxypiperidine(PAA-MPN)

2-propanol (9 g), di-tert-butyl dicarbonate (0.56 g; 0.003 mol), 5% palladium-carbon (0.2 g) containing 50% water, and 1-(1-benzyl-4-piperidylacetyl) mesyloxypiperidine (1.0 g; 0.003 mol) obtained in step 5 were applied to an autoclave (volume of 200 mL), and the mixture was reacted under a hydrogen pressure of 0.5 MPa for 4 hours at 45° C. The reaction mixture was cooled to room temperature, and the catalyst was filtered off. 2-Propanol was removed by concentration under reduced pressure, and toluene and brine were added and it was subjected to extraction and separation. The obtained organic layer was concentrated under reduced pressure. Toluene (4 g) was added to the concentrated residue and the mixture was ice-cooled, and the precipitated crystal was collected by filtration. The wet crystal was dried under reduced pressure to obtain 0.77 g of the above-referenced compound as a white crystalline powder (yield 74.6%). As a result of liquid chromatography analysis, the target compound was 98.4% and WPA-MPN was 0.03%.

Comparative Example 1

Synthesis of 1-(1-tert-butoxycarbonyl-4-piperidylacetyl)-4-mesyloxypiperidine(PAA-MPN)

The procedure of Example 1 was repeated except that steps [2] and [3] were not performed. WPA-MPN in the obtained PAA-MPN was 1.2%.

1-BPAE obtained in the step [1] of Example 1 and Comparative Example 1 was analyzed by gas chromatography. As a result, 1-BPAE was 98.1% and 0.8% of EPNA was contained therein as a by-product. Further, the toluene layer obtained by the steps [2] and [3] of Example 1 was analyzed by gas chromatography, and as a result EPNA was not detected.

It is considered that 1-BPAE reacts with a few amount of EPNA contained therein, and WPA-MPN is produced by the reaction process shown in the above reaction scheme [8].

Examples 2 to 6

In these Examples, a method for removing EPNA from 1-BPAE containing EPNA was examined.

An extraction solvent (4 g) and 1-BPAE (1.0 g) containing EPNA (0.9% of area percentage by gas chromatograph) to applied to a two-necked flask (20-mL of volume). 10% ammonium chloride aqueous solution (2 g) was added thereto, and the whole was subjected to extraction and separation, and a content of EPNA was examined in the obtained organic layer. In Example 2, toluene was used as an extraction solvent, hexane was used in Example 3, AcOEt (ethyl acetate) was used in Example 4, MTBE (methyl-tert-butyl ether) was used in Example 5, and $CHCl_3$ (chloroform) was used in Example 6. The results are shown in Table 1. EPNA could be efficiently removed using any of the extraction solvents.

TABLE 1

| Example | Extraction solvent | Area percentage by gas chromatograph (excluding solvent) (%) | |
|---|---|---|---|
| | | EPNA | 1-BPAE |
| Example 2 | Toluene | Not detected | 99.1 |
| Example 3 | Hexane | Not detected | 99.1 |
| Example 4 | AcOEt | Not detected | 99.0 |
| Example 5 | MTBE | Not detected | 99.0 |
| Example 6 | CHCl$_3$ | 0.1 | 98.8 |

Examples 7 to 13

Toluene (4 g) as the extraction solvent and 1-BPAE (1.0 g) containing EPNA (0.9% of area percentage by gas chromatograph) to applied to a two-necked flask (20-mL of volume). 10% ammonium chloride aqueous solution (2 g) was added thereto, and the whole was subjected to extraction and separation, and a content of EPNA was examined in the obtained organic layer. In Example 7, an HCl aqueous solution was added to the 10% ammonium chloride aqueous solution to adjust pH 2 and the whole was subjected to extraction and separation. Similarly, in Examples 8 to 13, the pH was adjusted to 2 to 8 using an aqueous solution of HCl or NH$_3$. The results are shown in Table 2. When using an ammonium chloride aqueous solution, EPNA could be removed efficiently at any pH.

TABLE 2

| Example | pH of 10% HH$_4$Cl aqueous solution | Area percentage by gas chromatograph (excluding solvent) (%) | |
|---|---|---|---|
| | | EPNA | 1-BPAE |
| Example 7 | 2.00 | Not detected | 99.1 |
| Example 8 | 3.00 | Not detected | 99.0 |
| Example 9 | 4.00 | Not detected | 99.0 |
| Example 10 | 5.00 | Not detected | 99.0 |
| Example 11 | 6.00 | Not detected | 99.0 |
| Example 12 | 7.00 | Not detected | 99.0 |
| Example 13 | 8.00 | 0.0 | 98.8 |

Comparative Examples 2-7

Toluene (4 g) as the extraction solvent and 1-BPAE (1.0 g) containing EPNA (0.9% of area percentage by gas chromatograph) to applied to a two-necked flask (20-mL of volume). In Comparative Example 2, water wherein pH was preliminary adjusted to 3.00 using an HCl aqueous solution, was added thereto, and the whole was subjected to extraction and separation. Similarly, in Comparative Examples 3 to 7, water wherein pH was adjusted to 4 to 8 using an HCl aqueous solution or a sodium hydroxide aqueous solution of, was added thereto, and the whole was subjected to extraction and separation. A content of EPNA was examined in the obtained organic layer. The results are shown in Table 3. It was difficult to efficiently remove EPNA without using an ammonium chloride aqueous solution.

TABLE 3

| Example | pH of 10% HH$_4$Cl aqueous solution | Area percentage by gas chromatograph (excluding solvent) (%) | |
|---|---|---|---|
| | | EPNA | 1-BPAE |
| Comparative Example 2 | 3.00 | 0.6 | 98.4 |
| Comparative Example 3 | 4.00 | 0.7 | 98.3 |
| Comparative Example 4 | 5.00 | 0.7 | 98.3 |
| Comparative Example 5 | 6.00 | 0.7 | 98.3 |
| Comparative Example 6 | 7.00 | 0.7 | 98.3 |
| Comparative Example 7 | 8.00 | 0.7 | 98.3 |

Referential Example 2

In this Referential Example, WPA-MPN was synthesized.

Step 1

Synthesis of (1-(1-tert-butoxycarbonyl-4-piperidylacetyl)-4-(2-(4-hydroxypiperidine1-yl)-2-oxyethyl) Piperidine 1-tert-butoxycarbonyl-4-piperidyl acetic acid (22.5 g; 0.093 mol) and dichloromethane (113 g) were applied to a reaction flask (volume of 300 mL), and then 1-ethyl-3-(3-dimethylaminopropyl)carbodiimide hydrochloride (18.1 g; 0.095 mol) was added thereto at 10° C. or less. 1-(4-piperidylacetyl)-4-hydroxypiperidine (21.0 g; 0.093 mol) synthesized according to JP Patent No. 4207201 was added thereto at 20° C., and the mixture was reacted at the same temperature for 5 hours. The obtained reaction mixture was brought to room temperature, and washed with water containing 1% hydrochloric acid. The obtained organic layer was concentrated under reduced pressure to obtain 38.2 g of the above-referenced compound as a colorless oil (yield 91.0%).

$^1$HNMR(CDCl$_3$) δ(ppm): 1.12 (m, 4H), 1.45 (s, 9H), 1.48 (m, 1H), 1.72 (d, J=12.5 Hz, 2H), 1.78 (d, J=12.9 Hz, 1H), 1.86 (d, J=11.3 Hz, 3H), 1.97 (m, 1H), 2.10 (m, 1H), 2.24 (d, J=6.7 Hz, 4H), 2.27 (m, 1H), 2.58 (t, J=12.5 Hz, 1H), 2.72 (t, J=11.0 Hz, 2H), 2.90 (s, 1H), 3.04 (t, J=11.9 Hz, 1H), 3.22 (m, 2H), 3.73 (m, 1H), 3.85 (d, J=13.7 Hz, 1H), 3.93 (s, 1H), 4.06 (m, 3H), 4.61 (d, J=13.3 Hz, 1H)

$^{13}$CNMR(CDCl$_3$) δ(ppm): 28.33, 31.99, 32.07, 32.83, 33.13, 33.15, 33.78, 34.45, 34.48, 38.88, 38.91, 39.16, 39.43, 41.83, 42.84, 42.87, 45.89, 66.58, 66.63, 79.24, 154.75, 169.57, 169.82

Step 5

Synthesis of (1-(1-tert-butoxycarbonyl-4-piperidylacetyl)-4-(2-(4-mesyloxypiperidine yl)-2-oxyethyl) Piperidine (1-(1-tert-butoxycarbonyl-4-piperidylacetyl)-4-(2-(4-hydroxypiperidine1-yl) oxyethyl) piperidine (30.0 g; 0.066 mol)) obtained in step 1 of Referential Example 2, triethylamine (8.74 g; 0.086 mol), and toluene (254 g) were applied to a reaction flask (volume of 500 mL), and then mesyl chloride (7.61 g; 0.066 mol) was added thereto at 10° C. or less, and the mixture was reacted at the same temperature for 5 hours. The obtained reaction mixture was brought to room temperature, and washed with brine. The obtained organic layer was concentrated under reduced pressure to obtain the above-referenced compound as a colorless oil. After purification by column chromatography, the crystals precipitated with toluene were collected by filtration. The wet crystal was dried under reduced pressure to obtain 20.5 g of the above-referenced compound as a white crystalline powder (yield 58.3%). The analysis results of liquid chromatography of the obtained compound were the same as those of WPA-MPN (i.e. by-product) contained in PAA-MPN in Example 1 and Comparative Example 1.

$^1$HNMR(CDCl$_3$) δ(ppm): 1.12 (m, 4H), 1.45 (s, 9H), 1.72 (d, J=12.5 Hz, 2H), 1.78 (d, J=14.9 Hz, 1H), 1.86 (m, 3H), 1.98 (m, 3H), 2.10 (m, 1H), 2.24 (d, J=7.0 Hz, 2H), 2.27 (m, 2H), 2.58 (t, J=12.9 Hz, 1H), 2.72 (t, J=12.3 Hz, 2H), 3.03 (m, 1H), 3.06 (s, 3H), 3.41 (m, 1H), 3.57 (m, 1H), 3.68 (m, 1H), 3.85 (d, J=12.5 Hz, 2H), 4.08 (br, 2H), 4.64 (d, J=13.3 Hz, 1H), 4.95 (m, 1H)

$^{13}$CNMR(CDCl$_3$) δ(ppm): 28.34, 31.26, 32.00, 32.11, 32.25, 32.84, 33.03, 33.16, 38.07, 38.70, 39.10, 39.42, 41.75, 41.99, 43.77, 45.82, 76.58, 79.15, 154.72, 169.60, 169.73

Mass spectrometry (EI): 530 (M+H)

INDUSTRIAL APPLICABILITY 1-(1-tert-butoxycarbonyl-4-piperidylacetyl)-4-mesyloxypiperidine obtained by the preparation method of the present invention is useful for an intermediate for synthesizing medicine

The invention claimed is:
1. A method for preparing 1-(1-benzyl-4-piperidylacetyl)-4-hydroxypiperidine, comprising the steps of:
(1) reductively reacting 1-benzyl-4-piperidylidene acetic acid ethyl ester represented by the formula [1]:

[Chem. 1]

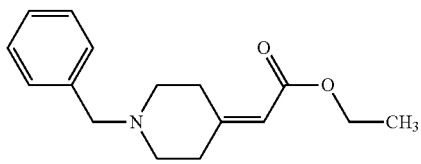

to obtain 1-benzyl-4-piperidyl acetic acid ethyl ester represented by the formula [2]:

[Chem. 2]

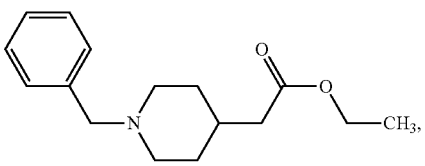

(2) adding an ammonium chloride aqueous solution and an organic solvent to a liquid containing 1-benzyl-4-piperidyl acetic acid ethyl ester, mixing the whole, and separating into an organic layer and an aqueous layer,
(3) collecting 1-benzyl-4-piperidyl acetic acid ethyl ester from the organic layer, and (4) reacting the obtained 1-benzyl-4-piperidyl acetic acid ethyl ester with 4-hydroxypiperidine represented by the formula [3]:

[Chem. 3]

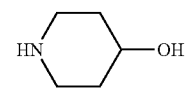

in the presence of base, to obtain 1-(1-benzyl-4-piperidylacetyl)-4-hydroxypiperidine represented by the formula [4]:

[Chem. 4]

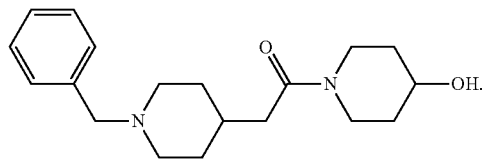

2. The method for preparing 1-(1-benzyl-4-piperidylacetyl)-4-hydroxypiperidine according to claim 1, wherein the organic solvent is selected from the group consisting of a hydrocarbon-based organic solvent, an ester-based organic solvent, an ether-based organic solvent, and halogen-based organic solvent.

3. A method for preparing 1-(1-tert-butoxycarbonyl-4-piperidylacetyl)-4-mesyloxypiperidine, comprising the steps of:
steps (1) to (4) according to claim 1, and
(5) reacting 1-(1-benzyl-4-piperidylacetyl)-4-hydroxypiperidine obtained in the step (4) with mesyl chloride in the presence of base, to obtain 1-(1-benzyl-4-piperidylacetyl)-4-mesyloxypiperidine represented by the formula [5]:

[Chem. 5]

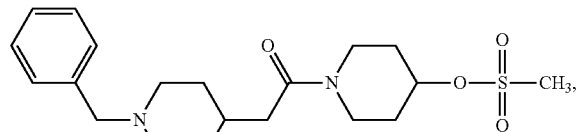

and
(6) reacting the 1-(1-benzyl-4-piperidylacetyl)-4-mesyloxypiperidine with di-tert-butyl dicarbonate in the presence of hydrogen and a catalyst containing palladium, to obtain 1-(1-tert-butoxycarbonyl-4-piperidylacetyl)-4-mesyloxypiperidine represented by the formula [6]:

[Chem. 6]

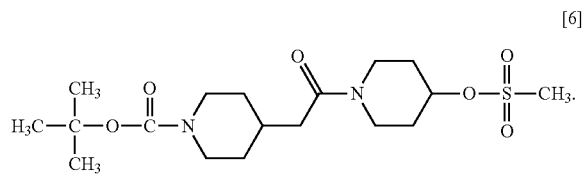

4. The method for preparing 1-(1-tert-butoxycarbonyl-4-piperidylacetyl)-4-mesyloxypiperidine according to claim 3, wherein the organic solvent is selected from the group consisting of a hydrocarbon-based organic solvent, an ester-based organic solvent, an ether-based organic solvent, and halogen-based organic solvent.

5. A method for collecting 1-benzyl-4-piperidyl acetic acid ethyl ester, comprising the steps of:

(1) reductively reacting 1-benzyl-4-piperidylidene acetic acid ethyl ester represented by the formula [1]:

[Chem. 7]

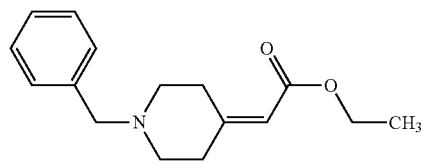

to obtain 1-benzyl-4-piperidyl acetic acid ethyl ester represented by the formula [2]:

[Chem. 8]

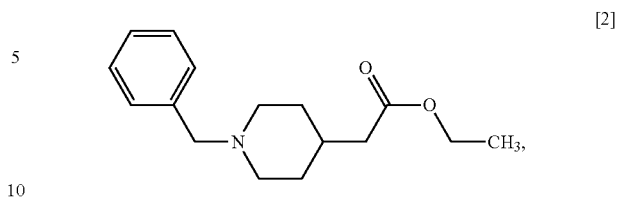

(2) adding an ammonium chloride aqueous solution and an organic solvent to the reaction mixture of 1-benzyl-4-piperidyl acetic acid ethyl ester, mixing the whole, and separating into an organic layer and an aqueous layer, and (3) collecting 1-benzyl-4-piperidyl acetic acid ethyl ester from the organic layer.

6. The method for collecting 1-benzyl-4-piperidyl acetic acid ethyl ester according to claim 5, wherein the organic solvent is selected from the group consisting of a hydrocarbon-based organic solvent, an ester-based organic solvent, an ether-based organic solvent, and halogen-based organic solvent.

7. 1-(1-tert-butoxycarbonyl-4-piperidylacetyl)-4-mesyloxypiperidine represented by the formula [6]:

[Chem. 10]

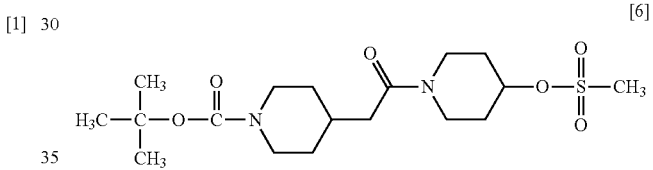

wherein a content of (1-(1-tert-butoxycarbonyl-4-piperidylacetyl)-4-(2-(4-mesyloxypiperidine-1-yl)-2-oxyethyl) piperidine represented by the formula [7]:

[Chem. 9]

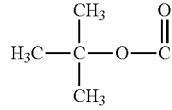

is 1.0% or less.

* * * * *